United States Patent
Liu et al.

(10) Patent No.: US 8,498,837 B2
(45) Date of Patent: Jul. 30, 2013

(54) PARAMAGNETISM-BASED REMOTE TEMPERATURE MEASUREMENT METHOD FOR MAGNETIC NANOPARTICLE

(75) Inventors: Wenzhong Liu, Wuhan (CN); Jing Zhong, Wuhan (CN); Yin Li, Wuhan (CN); Zhongzhou Du, Wuhan (CN); Di Xie, Wuhan (CN)

(73) Assignee: Huazhong University of Science and Technology (CN)

( * ) Notice: Subject to any disclaimer, the term of this patent is extended or adjusted under 35 U.S.C. 154(b) by 0 days.

(21) Appl. No.: 13/505,742

(22) PCT Filed: Mar. 28, 2011

(86) PCT No.: PCT/CN2011/072207
§ 371 (c)(1),
(2), (4) Date: May 2, 2012

(87) PCT Pub. No.: WO2012/119329
PCT Pub. Date: Sep. 13, 2012

(65) Prior Publication Data
US 2012/0239341 A1  Sep. 20, 2012

(51) Int. Cl.
*G01K 7/00* (2006.01)
(52) U.S. Cl.
USPC .......................................... 702/130; 977/838
(58) Field of Classification Search
USPC .......................................... 702/130; 977/838
See application file for complete search history.

(56) References Cited

U.S. PATENT DOCUMENTS

| | | | |
|---|---|---|---|
| 2009/0068114 A1 | 3/2009 | Haik | 424/9.32 |
| 2010/0327869 A1* | 12/2010 | Kim et al. | 324/309 |
| 2011/0098558 A1 | 4/2011 | Weaver et al. | |

FOREIGN PATENT DOCUMENTS

| | | |
|---|---|---|
| CN | 101352342 | 1/2009 |
| CN | 101601607 | 12/2009 |
| DE | 102008049605 | 12/2009 |
| JP | 3333875 | 10/2002 |
| WO | 2009088062 | 7/2009 |

OTHER PUBLICATIONS

Rajendran, "Engineering Physics" (2009).*
Chen et al., "Size determination of superparamagnetic nanoparticles from magnetization curve," J, of Applied Physics (2009).*
Wang et al., "A superferromagnetic approach for rapidly quenched Y60Fe30AI10 alloys," J. Phys,: Condens. Matter (2000).*
PCT International Search Report for PCT/CN2011/072207 filed Mar. 28, 2011 in the name of Huazhong University of Science and Technology.
PCT Written Opinion for PCT/CN2011/072207 filed Mar. 28, 2011 in the name of Huazhong University of Science and Technology.
English translation of PCT Written Opinion for PCT/CN2011/072207 filed Mar. 28, 2011 in the name of Huazhong University of Science and Technology.

(Continued)

*Primary Examiner* — Sujoy Kundu
*Assistant Examiner* — Hyun Park
(74) *Attorney, Agent, or Firm* — Wenhua Yu (57) ABSTRACT

The invention discloses a paramagnetism-based remote temperature measurement method for magnetic nanoparticles, and the method comprises: applying multiple times of excited magnetic fields on the area of a magnetic nano sample, constructing an equation group between the different excited magnetic fields and corresponding magnetic susceptibilities according to the Langevin's paramagnetic theorem, and obtaining the information of temperature and sample concentration via the equation group. The invention is capable of more precisely and more quickly detecting the temperature of an object, and especially applicable for the detection of thermal motion at bio-molecular level. Experiments indicate the measurement error is less than 0.56K.

6 Claims, 10 Drawing Sheets

OTHER PUBLICATIONS

Wang et al., Magnetic Susceptibility in Different Field of Quasi-One Dimensional 1/2s Spin Ladder Compound Sr14-xCaxCu24O41, Chinese Journal of Low Temperature Physics, 2007, 29(3): 173-178.

Zhong, J, et al., "A noninvasive, remote and precise method for temperature and concentration estimation using magnetic nanoparticles," Nanotechnology 2012 (23) 075703 (9pp).

* cited by examiner (a)

FIG. 10

PARAMAGNETISM-BASED REMOTE TEMPERATURE MEASUREMENT METHOD FOR MAGNETIC NANOPARTICLE

FIELD OF THE INVENTION

The invention relates to a nano measurement field, and more particularly to a temperature measurement method based on magnetic susceptibility of nano superparamagnetic materials.

BACKGROUND OF THE INVENTION

Temperature information deeply inside objects, especially deeply in vivo, is limited by physical principle of time and space, and information transportation, and this makes it impossible to facilitate non-contact temperature measurement within 1000° C. Temperature is direct evidence that characterizes immune response and life activities. Hyperthermia cancer therapy expects to control temperature at cancerization parts at 45° C.-47° C. during hyperthermia process. Normally 45° C.-47° C. is a critical temperature point that ensures safety of normal cells and causes cancer cells necrosis gradually. Remote detection of temperature field information of cancer cells between lungs and livers are critical for breakthrough of the hyperthermia therapy. However, internal organs, bones, vessels or skin are a natural barrier for the temperature information. In other fields, temperature distribution at outlets of aero engines directly affect lifetime of turbines, fast measurement methods are to greatly improve performance of engines without changing temperature distribution field of turbines. Therefore, a more popularly used method for measuring temperature at deep sites of objects becomes a key technique for promoting development of biomedical and industrial fields.

Technically, it is comparatively difficult to apply the existing temperature measurement technique to temperature measurement of deep sites of objects. The magnetic resonance temperature measurement technique brings twilight for temperature field measurement of human beings, and it is difficult to apply the magnetic resonance temperature measurement to vivo (such as hyperthermia cancer therapy) temperature measurement. However, too weak magnetic property of molecular directly or indirectly leads to technical difficulty of measurement. Temperature characteristic parameters of hydrogen molecular in vivo cannot be pre-obtained, and during test, measurement of temperature difference is implementing by measuring the same point for two times before and after heating, and at the same time, a test point is required to be highly static, which form a main source of error. Researchers notice that magnetic moments of magnetic nanoparticles (tri-iron tetroxide) are three orders of magnitude higher than nuclear magnetic signals of hydrogen molecules soon. Thus, the nano magnetic measurement system is expected to achieve high speed and high signal-noise ratio. J. B. Weaver from America made useful exploration of the nano magnetism, and he used the ratio between the triple harmonic generation and the quintuple harmonic generation after AC magnetization using nano superparamagnetic materials for experiment, and the precision obtained was greater than 1 degree in a range of 20° C. to 50° C. Temperature-related constants of the magnetic nanoparticles, such as size, saturation magnetic moment and so on can be precisely and repeatedly pre-measured outside vivo, and magnetic parameters can be predetermined. Uncertainty of concentration distribution and space distribution of magnetic nanoparticles in vivo is to cause very large error of temperature measurement in vivo. Uncertainty of pixel distribution in vivo causes temperature of nuclear magnetic resonance can only implement measurement of temperature difference.

SUMMARY OF THE INVENTION

It is an objective of the invention to provide a paramagnetism-based remote temperature measurement method for a magnetic nanoparticle that is capable of precisely and quickly implementing remote temperature measurement of objects.

A paramagnetism-based remote temperature measurement method for a magnetic nanoparticle, comprising:
(1) positioning a magnetic nano sample at a measured object;
(2) applying n times of different excited magnetic fields on area of the magnetic nano sample;
(3) collecting magnetization of the magnetic nano sample under different excited magnetic fields, and calculating magnetic susceptibility under different excited magnetic fields according to the magnetization;
(4) constructing equations between magnetic susceptibility $\chi_i$ and excited magnetic fields $H_i$ of the magnetic nano sample $$\frac{1}{\chi_i} = \frac{H_i}{NML\left(\frac{MH_i}{kT}\right)}, i = 1, 2 \ldots n,$$

where reciprocal of the Langevin's function $$L\left(\frac{MH_i}{kT}\right): \frac{1}{L(\alpha)} = \sum_{j=0}^{J} c_{2j-1} \alpha^{2j-1}, \alpha = \frac{MH_i}{kT},$$

$c_{2j-1}$ is a polynomial coefficient, J+1 is a predetermined polynomial expansion term, N is concentration of the sample, M is atomic magnetic moment of the sample, k is a Boltzmann's constant, and T is temperature of the measured object;
(5) solving the equations whereby obtaining the temperature T.

Advantageously, J=1, step (5) comprises: using a linear equation $$\frac{1}{\chi_i} = 3x + \frac{1}{5}H_i^2 y$$

to perform curve fitting on a sequence point $$\left(H_i^2, \frac{1}{\chi_i}\right),$$

calculating the temperature according to an intercept 3x and a slope ⅕y of the straight line obtained by the curve fitting:

$$T = \frac{M}{k}\sqrt{\frac{x}{y}},$$

and calculating the concentration of the sample:

$$N = \frac{1}{M\sqrt{xy}}.$$

Advantageously, $2 \leq J \leq 5$, and step (5) comprises:

Firstly transforming the equation between the magnetic susceptibility $\chi_i$ and the excited magnetic fields $H_i$ into a matrix equation $$\begin{bmatrix} \frac{1}{\chi_1} \\ \frac{1}{\chi_2} \\ \vdots \\ \frac{1}{\chi_n} \end{bmatrix} = A \cdot \begin{bmatrix} \frac{1}{a} \\ \frac{b}{a} \\ \vdots \\ \frac{b^{Q-1}}{a} \end{bmatrix}, \text{ where } \begin{cases} a = \frac{M^2 N}{kT} \\ b = \frac{1}{M^2 N^2} \end{cases};$$

$1 \leq Q \leq J+1$, and A is a coefficient matrix;

Then solving equations $$\begin{cases} \frac{b^{q-1}}{a} = A_q^* \cdot \left[ \frac{1}{\chi_1} \frac{1}{\chi_2} \cdots \frac{1}{\chi_n} \right]^T, q = 1 \\ \frac{b^{q-1}}{a} = A_q^* \cdot \left[ \frac{1}{\chi_1} \frac{1}{\chi_2} \cdots \frac{1}{\chi_n} \right]^T, 2 \leq q \leq Q \end{cases}$$

whereby obtaining a and b, where $A_q^*$ is the $q^{th}$ row of a generalized inverse $A^*$ of the coefficient matrix A; and Finally calculating the temperature of the measured object:

$$T = \frac{M}{k\sqrt{b}},$$

and the concentration of the sample:

$$N = \frac{a}{M\sqrt{b}}.$$

Advantages of the invention comprise:

The invention provides a temperature measurement method based on the magnetic susceptibility of nano superparamagnetic materials, multiple (normally greater than two) times of excited magnetic fields are applied on area of a magnetic nano sample, equations between different excited magnetic fields and corresponding magnetic susceptibility are constructed according to the Langevin's paramagnetic theorem, and information of temperature and sample concentration are obtained via the equations.

The invention makes it possible for implementing precise and quick temperature detection of objects, and especially applicable for detection of thermal motion at biomolecular level. Different from hydrogen molecular sensors used in the MRI technique, the nano magnetic temperature measurement method employs nano superparamagnetic materials in magnetohyperthermia cancer therapy as temperature sensors, and has advantages in many aspects. Magnetic susceptibility measurement is not relaxation response but instant measurement, and therefore features good real-time performance. Constants of magnetic nanoparticles relating to temperature, such as size, saturation magnetic moment and so on are precisely and repeatedly measured outside the object, and magnetic parameters are predetermined. Meanwhile, magnetic moments of the magnetic nanoparticles (tri-iron tetroxide) are three orders of magnitude higher than nuclear magnetic signals of hydrogen molecules. Therefore, a nano magnetic measurement system can implement high speed and a high signal-noise ratio. Average error of the temperature measurement technique after 9 times' repetition is less than 0.56K. Temperature measurement error less than 1K can meet requirement in the hyperthermia cancer therapy for temperature measurement precision. Application prospect of the invention is to implement a temperature measurement technique that can be applied deeply in an object comprising the vivo, and is below the Curie temperature of iron-magnetic materials.

BRIEF DESCRIPTION OF THE DRAWINGS

FIG. 1(a) illustrates the linear prediction model, and FIG. 1(b) illustrates the polynomial prediction model;

FIG. 2(a) illustrates affect on the linear prediction model, and FIG. 2(b) illustrates affect on the polynomial prediction model;

FIG. 8(a) is a curve between a preset (theoretical) temperature value TT and a measured temperature value ETN during one measurement, and FIG. 8(b) illustrates temperature error during the measurement;

FIG. 9(a) is a curve between an average temperature value and actual temperature after 9 times of measurement, and FIG. 9(b) illustrates difference between the average value and a preset theoretical value;

FIG. 10(b) illustrates difference between the test results and the actual results at different temperatures.

SPECIFIC EMBODIMENTS

1. Theoretical Basis

Superparamagnetic materials follow the Langevin's function:

$$I = NM\left(\frac{e^\alpha + e^{-\alpha}}{e^\alpha - e^{-\alpha}} - \frac{1}{\alpha}\right) = NM\left(\coth\alpha - \frac{1}{\alpha}\right)$$

where I is magnetization, N is the number of particles per unit volume, M is atomic magnetic moment, is the Langevin's function, in this function $$\alpha = \frac{MH}{kT},$$

K is the Boltzmann's constant, T is absolute temperature.

The magnetic susceptibility $\chi$ follows equation:

$$\frac{1}{\chi} = \frac{H}{I} = \frac{H}{NML(\alpha)}$$

A reciprocal of the Langevin's function is $$\frac{1}{L(\alpha)} = \sum_{j=0}^{J} c_{2j-1}\alpha^{2j-1},$$

where $c_{2j-1}$ is a polynomial coefficient, and J+1 is a predetermined polynomial expansion term.

2. Solution

1) Linear Approximation Model of the Langevin's Paramagnetic Theorem:

Assuming J=1, $$\frac{1}{\chi} = \frac{H}{I} = \frac{H}{NML(\alpha)} \approx \frac{H}{NM}\left(\frac{3}{\alpha} + \frac{\alpha}{5}\right),$$

where $\chi$ is magnetic susceptibility,

By replacing $$\alpha = \frac{MH}{kT}$$

in the above equation:

$$\frac{1}{\chi} \approx \frac{3kT}{NM^2} + \frac{H^2}{5NkT}$$

By setting different excited magnetic fields $H_i$ (i=1, 2 ... n), the equation is formulated as:

$$\begin{cases} \frac{1}{\chi_1} = \frac{3kT}{NM^2} + \frac{H_1^2}{5NkT} \\ \frac{1}{\chi_2} = \frac{3kT}{NM^2} + \frac{H_2^2}{5NkT} \\ \vdots \\ \frac{1}{\chi_n} = \frac{3kT}{NM^2} + \frac{H_n^2}{5NkT} \end{cases}$$

Under moderate intensity, a magnetic susceptibility reciprocal—temperature curve varies, and the curve does not pass an absolute temperature zero point 0 K predicted by the Curie's law, or a fixed Curie point θ described in the Curie-Weiss law. Within certain temperature range, intercept shift exists on the magnetic susceptibility reciprocal—temperature curve, and the shift is related to intensity of the excited magnetic field. This phenomena is defined as magnetic modulation property of the magnetic susceptibility reciprocal—temperature curve. The magnetic modulation property of the magnetic susceptibility reciprocal—temperature curve indicates that under moderate intensity, the magnetic nanoparticles no longer follow the Curie's paramagnetic law.

Assuming $$\begin{cases} MN = \frac{1}{\sqrt{xy}} \\ \frac{T}{M} = \frac{1}{k}\sqrt{\frac{x}{y}} \end{cases}$$

namely substituting $$\begin{cases} x = \frac{kT}{M^2N} \\ y = \frac{1}{kTN}, \end{cases}$$

in the equation:

$$\begin{cases} \frac{1}{\chi_1} = 3x + \frac{1}{5}H_1^2 y \\ \frac{1}{\chi_2} = 3x + \frac{1}{5}H_2^2 y \\ \vdots \\ \frac{1}{\chi_n} = 3x + \frac{1}{5}H_n^2 y \end{cases}$$

where $H_n$ and $\chi_n$ are both known quantities which can be obtained by instrumental measurement, curve fitting is performed on a sequence point $$\left(H_i^2, \frac{1}{\chi_i}\right)$$

by using a linear equation $$\frac{1}{\chi_i} = 3x + \frac{1}{5}H_i^2 y,$$

and temperature T and concentration are respectively calculated according to an intercept $3x$ and a slope $\frac{1}{5}y$ of a line after curve fitting:

$$T = \frac{M}{k}\sqrt{\frac{x}{y}},$$

$$N = \frac{1}{M\sqrt{xy}}.$$

2) Polynomial Approximation Model of the Langevin's Paramagnetic Theorem:

assuming $J \geq 2$ $$\frac{1}{\chi} = \frac{3kT}{NM^2} + \frac{1}{5}\frac{H^2}{NkT} - \frac{M^2 H^4}{175 k^3 NT^3} + \frac{2M^4 H^6}{7875 k^5 NT^5} - \frac{37 M^6 H^8}{3031875 k^7 NT^7} \cdots$$

By setting different excited magnetic fields $H_i$ (i=1, 2 … n), the equation is formulated as:

$$\begin{cases} \frac{1}{\chi_1} = 3x + \frac{1}{5}H_1^2 y - \frac{H_1^4 y^2}{175 x} + \frac{2H_1^6 y^3}{7875 x^2} - \frac{37 H_1^8 y^4}{3031875 x^3} \cdots \\ \frac{1}{\chi_2} = 3x + \frac{1}{5}H_2^2 y - \frac{H_2^4 y^2}{175 x} + \frac{2H_2^6 y^3}{7875 x^2} - \frac{37 H_2^8 y^4}{3031875 x^3} \cdots \\ \vdots \\ \frac{1}{\chi_n} = 3x + \frac{1}{5}H_n^2 y - \frac{H_n^4 y^2}{175 x} + \frac{2H_n^6 y^3}{7875 x^2} - \frac{37 H_n^8 y^4}{3031875 x^3} \cdots \end{cases}$$

Assuming $$\begin{cases} a = \frac{1}{x} = \frac{M^2 N}{kT} \\ b = \frac{x}{y} = \frac{1}{M^2 N^2}, \end{cases}$$

the equation is formulated as:

$$\begin{cases} \frac{a}{\chi_1} = 3 + \frac{1}{5}H_1^2 b - \frac{H_1^4}{175} b^2 + \frac{2H_1^6}{7875} b^3 - \frac{37 H_1^8}{3031875} b^4 \cdots \\ \frac{a}{\chi_2} = 3 + \frac{1}{5}H_2^2 b - \frac{H_2^4}{175} b^2 + \frac{2H_2^6}{7875} b^3 - \frac{37 H_2^8}{3031875} b^4 \cdots \\ \vdots \\ \frac{a}{\chi_n} = 3 + \frac{1}{5}H_n^2 b - \frac{H_n^4}{175} b^2 + \frac{2H_n^6}{7875} b^3 - \frac{37 H_n^8}{3031875} b^4 \cdots \end{cases}$$

The binary high overdetermined equation is rewritten as:

$$\begin{bmatrix} \frac{1}{\chi_1} \\ \frac{1}{\chi_2} \\ \vdots \\ \frac{1}{\chi_n} \end{bmatrix} = \begin{bmatrix} 3 & \frac{H_1^2}{5} & \frac{H_1^4}{175} & \frac{2H_1^6}{7875} & \frac{37 H_1^8}{3031875} & \cdots \\ 3 & \frac{H_2^2}{5} & \frac{H_2^4}{175} & \frac{2H_2^6}{7875} & \frac{37 H_2^8}{3031875} & \cdots \\ \vdots & \vdots & \vdots & \vdots & \vdots & \\ 3 & \frac{H_n^2}{5} & \frac{H_n^4}{175} & \frac{2H_n^6}{7875} & \frac{37 H_n^8}{3031875} & \cdots \end{bmatrix} \begin{bmatrix} \frac{1}{a} \\ \frac{b}{a} \\ \frac{b^2}{a} \\ \frac{b^3}{a} \\ \frac{b^4}{a} \\ \vdots \end{bmatrix}$$

If assuming $$A = \begin{bmatrix} 3 & \frac{H_1^2}{5} & \frac{H_1^4}{175} & \frac{2H_1^6}{7875} & \frac{37 H_1^8}{3031875} & \cdots \\ 3 & \frac{H_2^2}{5} & \frac{H_2^4}{175} & \frac{2H_1^6}{7875} & \frac{37 H_1^8}{3031875} & \cdots \\ \vdots & \vdots & \vdots & \vdots & \vdots & \\ 3 & \frac{H_n^2}{5} & \frac{H_n^4}{175} & \frac{2H_n^6}{7875} & \frac{37 H_n^8}{3031875} & \cdots \end{bmatrix}$$

$A^*$ is a generalized inverse of the matrix $A$, then $$A^* \begin{bmatrix} \frac{1}{\chi_1} \\ \frac{1}{\chi_2} \\ \vdots \\ \frac{1}{\chi_n} \end{bmatrix} = A^* A \begin{bmatrix} \frac{1}{a} \\ \frac{b}{a} \\ \frac{b^2}{a} \\ \frac{b^3}{a} \\ \frac{b^4}{a} \\ \vdots \end{bmatrix} = \begin{bmatrix} \frac{1}{a} \\ \frac{b}{a} \\ \frac{b^2}{a} \\ \frac{b^3}{a} \\ \frac{b^4}{a} \\ \vdots \end{bmatrix}.$$

Further, if $A_1^*, A_2^*, A_3^*, A_4^*$ are respectively the first to the fourth vectors of the matrix $A^*$, then $$\frac{1}{a} = A_1^* \begin{bmatrix} \frac{1}{\chi_1} & \frac{1}{\chi_2} & \cdots & \frac{1}{\chi_n} \end{bmatrix}^T \quad 1$$

$$\frac{b}{a} = A_2^* \begin{bmatrix} \frac{1}{\chi_1} & \frac{1}{\chi_2} & \cdots & \frac{1}{\chi_n} \end{bmatrix}^T \quad 2$$

$$\frac{b^2}{a} = A_3^* \begin{bmatrix} \frac{1}{\chi_1} & \frac{1}{\chi_2} & \cdots & \frac{1}{\chi_n} \end{bmatrix}^T \quad 3$$

$$\frac{b^3}{a} = A_4^* \begin{bmatrix} \frac{1}{\chi_1} & \frac{1}{\chi_2} & \cdots & \frac{1}{\chi_n} \end{bmatrix}^T \quad 4$$

In practice, a and b can be obtained by combining $$\frac{1}{a} \text{ with } \frac{b}{a}$$

in the first two equations, namely $$\begin{cases} a = \dfrac{1}{A_1^*\left[\dfrac{1}{\chi_1} \ \dfrac{1}{\chi_2} \ \cdots \ \dfrac{1}{\chi_n}\right]} \\ b = \dfrac{A_2^*\left[\dfrac{1}{\chi_1} \ \dfrac{1}{\chi_2} \ \cdots \ \dfrac{1}{\chi_n}\right]}{A_1^*\left[\dfrac{1}{\chi_1} \ \dfrac{1}{\chi_2} \ \cdots \ \dfrac{1}{\chi_n}\right]} \end{cases}$$

Equations ① and ② are combined as a first-degree polynomial approximation model, equations ① and ③ are combined as a second-degree polynomial approximation model, equations ① and ④ are combined as a third-degree polynomial approximation model, finally the first-stage, the second-stage, or the third-stage polynomial approximation model is solved to obtain a and b, and the equations $$\begin{cases} T = \dfrac{M}{k\sqrt{b}} \\ N = \dfrac{a}{M\sqrt{b}} \end{cases}$$

are used to calculate and obtain the temperature and the concentration (N, the number of particles per unit volume).

The above method uses the first to the fourth row vector of the matrix A* to construct the approximation model, and is a sample only, but the invention cannot be understood as only selecting the first four row vectors. A general construction mode of the approximation model is given as follows:

$$\begin{cases} \dfrac{b^{q-1}}{a} = A_q^* \cdot \left[\dfrac{1}{\chi_1} \ \dfrac{1}{\chi_2} \ \cdots \ \dfrac{1}{\chi_n}\right]^T, & q = 1 \\ \dfrac{b^{q-1}}{a} = A_q^* \cdot \left[\dfrac{1}{\chi_1} \ \dfrac{1}{\chi_2} \ \cdots \ \dfrac{1}{\chi_n}\right]^T, & 2 \le q \le Q \end{cases}, 1 \le Q \le J+1,$$

Expansion terms of the above polynomial model have no limitation, the invention uses three-term, four-term, five-term, six-term, and ten-term for operation, and calculation results indicate they can all implement the objective of the invention. However, the more the terms are, the easier pathological property of the equation may occur, therefore polynomials having three to six terms are suggested.

3. Simulation Example

1) Simulation Model and Test Explanation

To study effectiveness and optimization design of the temperature measurement method, simulation data containing noise are used to execute experimental test. Defaut samples (unless otherwise specified) during the measurement are EMG1400 (FerroTec, USA), magnetic moment of particles is set to $2.49 \times 10^{-17}$. A noise model uses an awgn function in MATLAB to directly apply noise with a preset signal-noise ratio on the magnetic moment during magnetization process. A signal-noise ratio of the magnetization curve is set to 100 dB to 200 dB according to different test targets. The magnetization curve is uniformly divided into 200 points from zero to the maximum value. Taken into account that more polynomial expansions are to increase the number of conditions of a matrix A in a binary overdetermined equation, and thus leading to pathological property of solution. This will cause solution of the equation to be very sensitive to noise. Therefore in polynominal expansion of the Langevin's equation, expansions of the first six terms are used.

Figure 1:
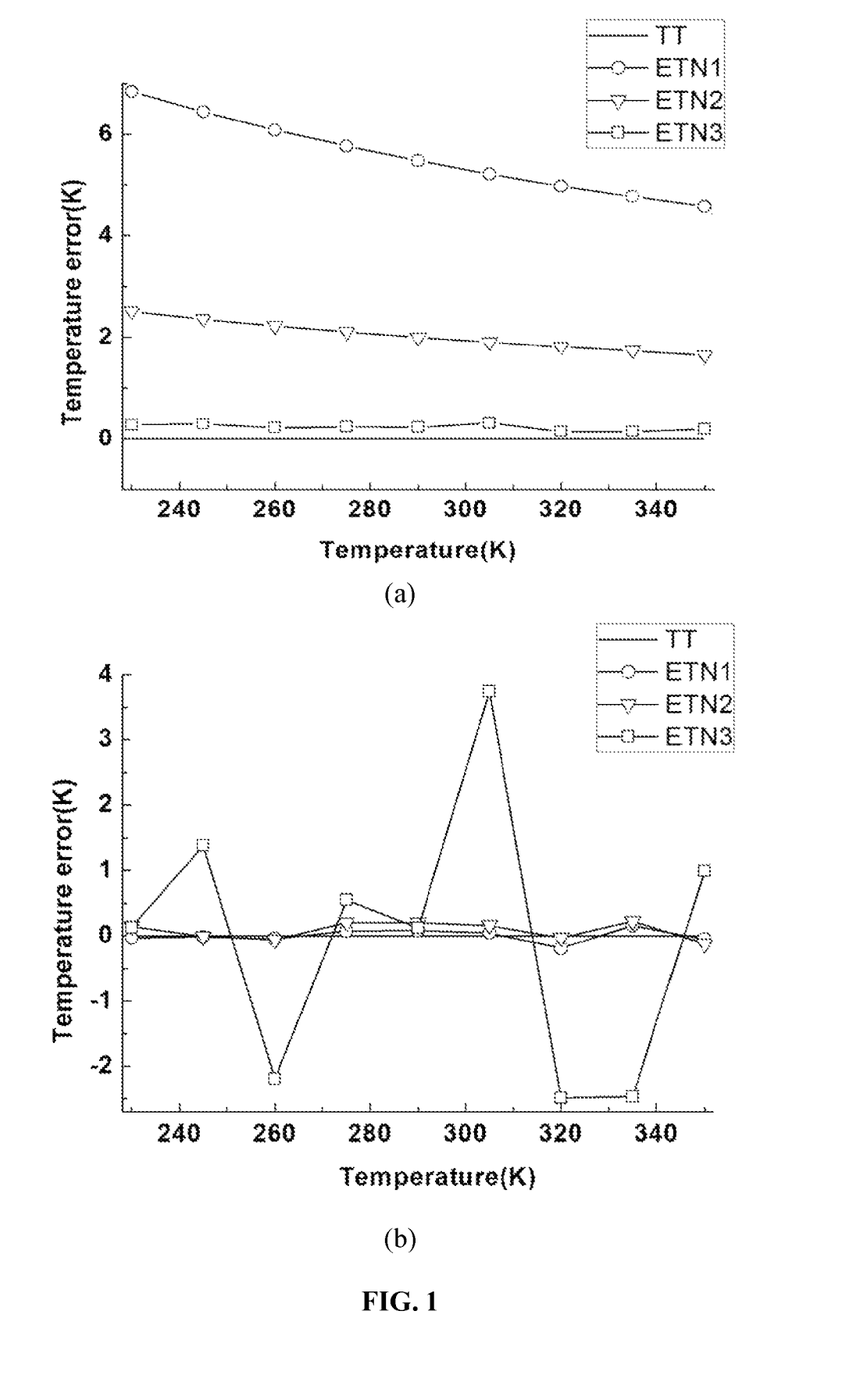
FIG. 1 illustrates relationship between variation of excited magnetic fields (maximum value) and temperature measurement errors of a linear prediction model and a polynomial prediction model.
Figure 2:
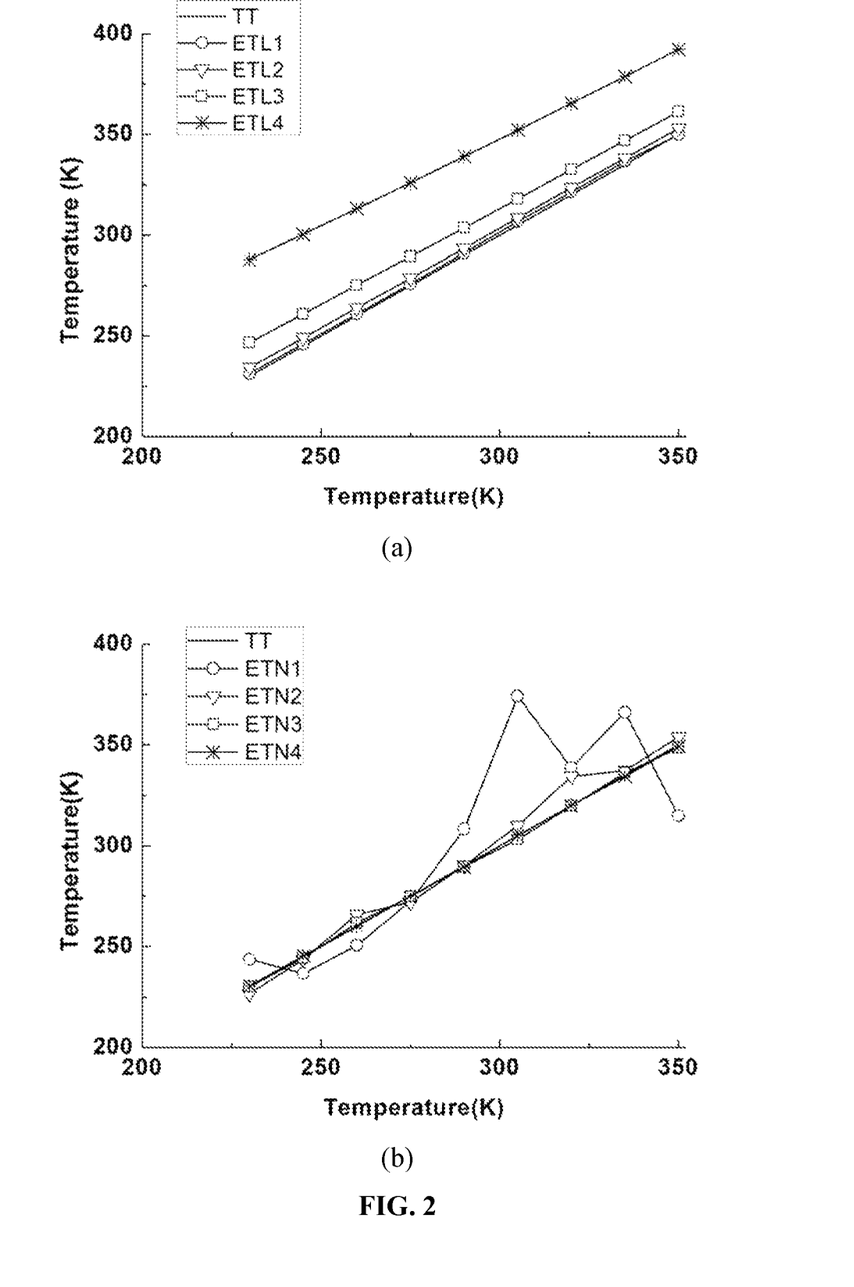
FIG. 2 illustrates affect of variation of saturation magnetic susceptibility on a linear prediction model and a polynomial prediction model.

FIGS. 1 to 9 study and analyze a linear approximation model and a polynomial approximation model, and further analyze a first-degree polynomial model method. FIGS. 1 and 2 compare and analyze the linear model and the polynomial model. FIG. 1 illustrates comparison results between variation of excited magnetic fields and the linear model and the polynomial model under a signal-noise ratio of 130 dB, temperature is 230K-350K, every 15K is one point. TT is a theoretical value under ideal condition. FIG. 1(a) illustrates affect of variation of the excited magnetic field (maximum value) on temperature measurement error of the linear prediction model, where the maximum excited magnetic fields of ETL1, ETL2 and ETL3 are respectively 1000 Gs, 600 Gs and 200 Gs. FIG. 1(b) illustrates affect of variation of the excited magnetic field (maximum value) on temperature measurement error of the polynomial prediction model, where the maximum excited magnetic fields of ETN1, ETN2 and ETN3 are respectively 1000 Gs, 600 Gs and 200 Gs. FIG. 2 illustrates affect of variation of saturation magnetic susceptibility on the linear prediction model and the polynomial prediction model under a simulated signal-noise ratio of 90 dB. TT is a theoretical value under ideal condition. FIG. 2(a) illustrates affect of variation of the saturation magnetic susceptibility on the linear prediction model. Saturation magnetic moments of the ETL1, ETL2, ETL3, ETL3 and ETL4 follow a sequence with a geometric proportional factor of 2. Saturation magnetic moment of an initial value ETL1 is $2.49 \times 10^{-17}$. FIG. 2(b) illustrates affect of variation of the saturation magnetic susceptibility on the polynomial prediction model. Saturation magnetic moments ETN1, ETN2, ETN3 and ETN4 are respectively the same as those of ETL1, ETN2, ETN3 and ETN4.

Figure 3:
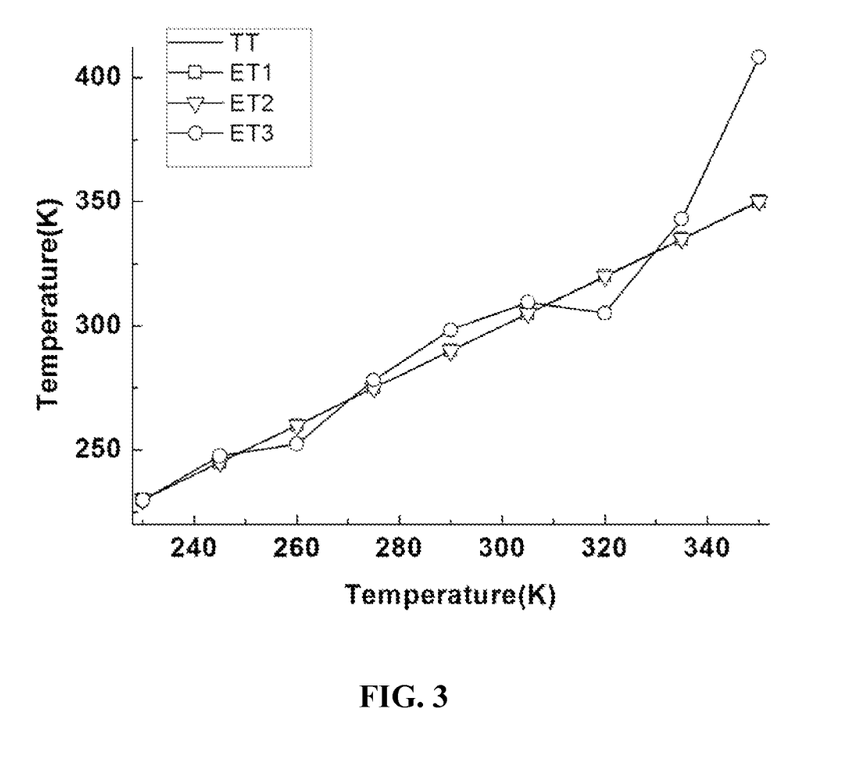
FIG. 3 illustrates temperature measurement results of a simulation magnetization curve based on −200 dB noise.
Figure 4:
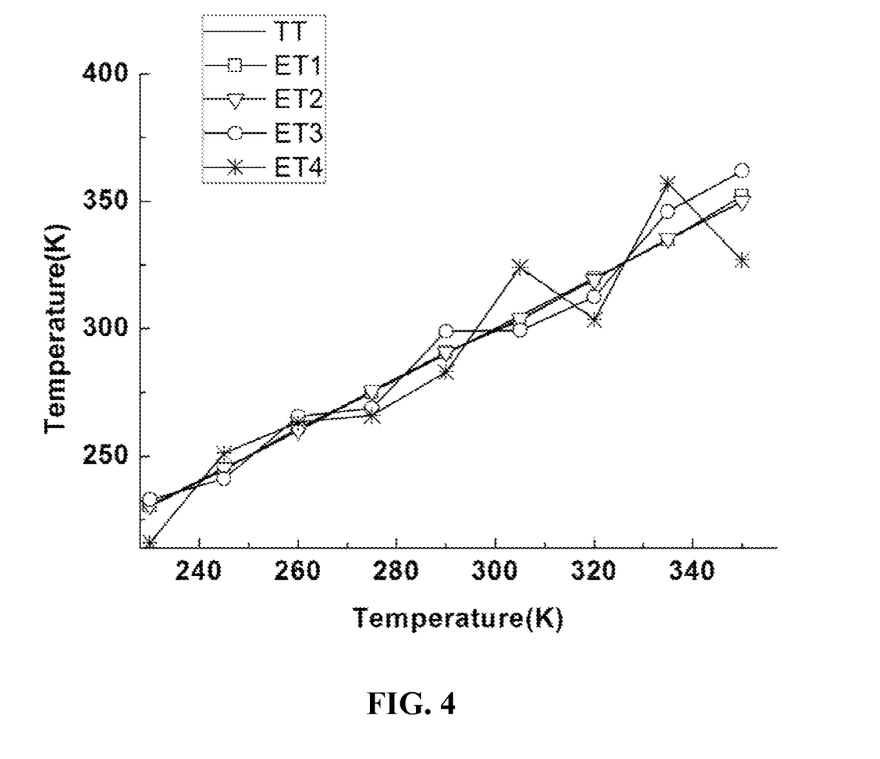
FIG. 4 illustrates results after employing a first-degree polynomial prediction algorithm.
Figure 5:
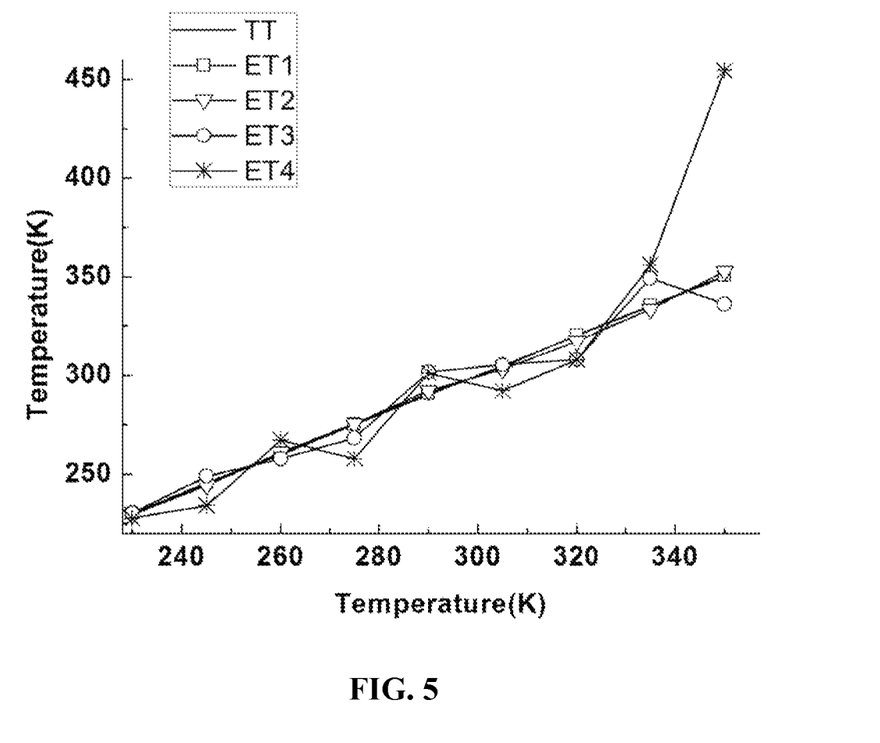
FIG. 5 illustrates results after employing a quadratic polynomial prediction algorithm.
Figure 6:
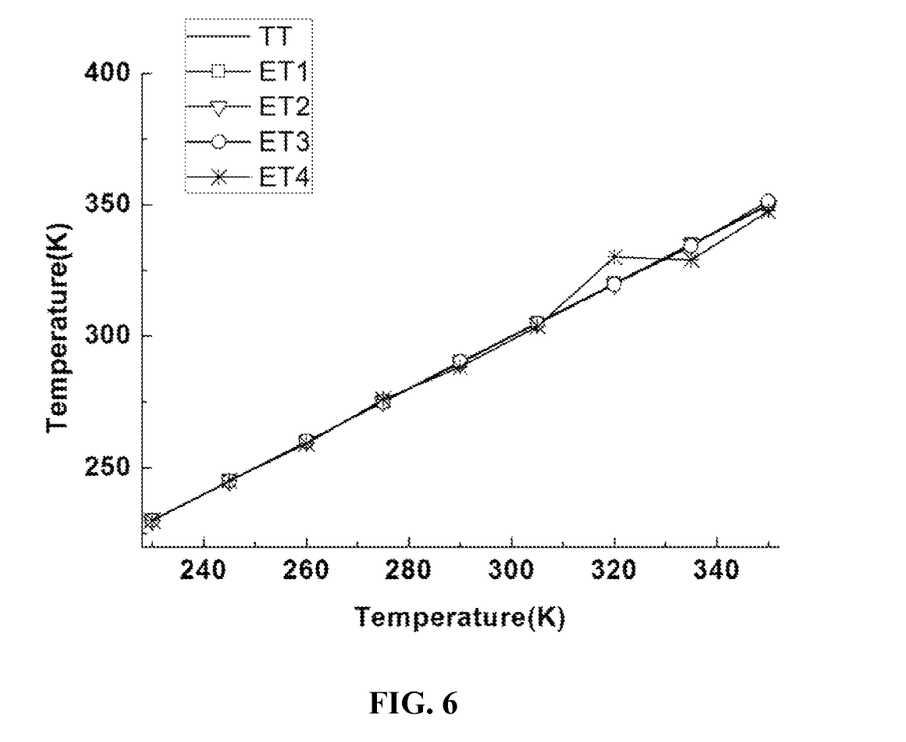
FIG. 6 illustrates results after employing a third-degree polynomial prediction algorithm.
Figure 7:
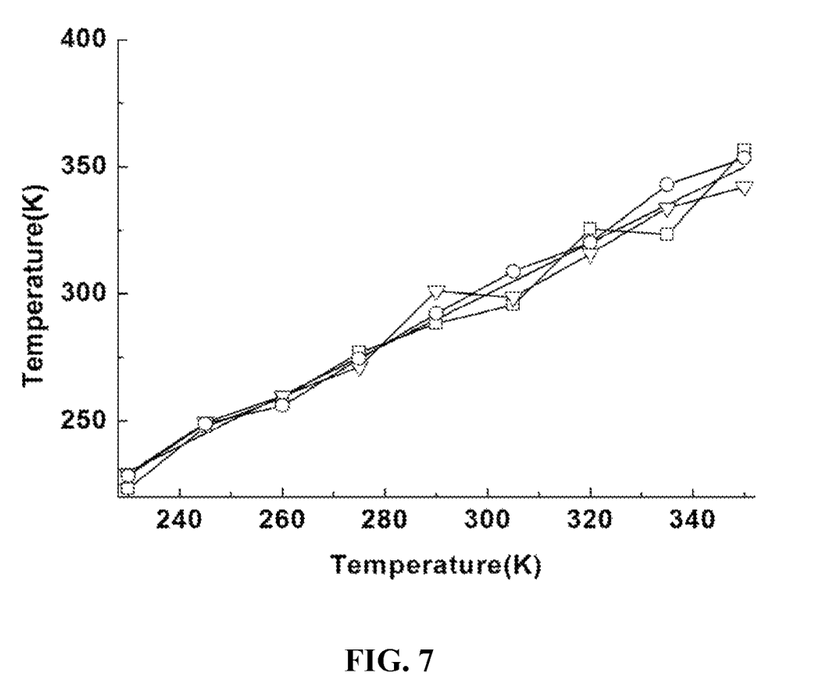
FIG. 7 illustrates multiple measurement results after employing a first-degree polynomial prediction algorithm based on simulation data of −110 dB noise.

FIGS. 3 to 7 illustrate comparison results of Taylor's expansions with different degrees in the polynomial model. FIG. 4 illustrates comparison results of the first-degree, second-degree and third-degree Taylor's expansions under a signal-noise ratio of 200 dB. ET3, ET2, ET1, and TT are respectively the third-degree, second-degree, first-degree polynomial, and a theoretical value. FIGS. 4 to 6 illustrate results of the first-degree, second-degree, third-degree Taylor's expansion under different signal-noise ratios. In FIG. 4, ET1, ET2, ET3, ET4, and TT are respectively −130 dB, −120 dB, −110 dB, and −100 dB noise prediction result, and a theoretical value. In FIG. 5, ET1, ET2, ET3, ET4, and TT are respectively −180 dB, −170 dB, −160 dB, −150 dB noise prediction results, and a theoretical value. In FIG. 6, ET1, ET2, ET3, ET4, and TT are respectively −230 dB, −220 dB, −210 dB, and −200 dB noise prediction result, and a theoretical value. FIG. 7 illustrate measurement data using the first-degree Taylor's expansion under a 100 dB signal-noise ratio.

Simulation Result and Discussion

Simulation data indicate as the signal-noise ratio is small enough, the above-mentioned temperature prediction model can facilitate any precision. For example, in FIG. 1, error between temperature prediction under comparatively small magnetic excitation and that under a high signal-noise ratio can be less than 0.01K. In FIG. 3, temperature measurement is performed under a signal-noise ratio of 200 dB, measured data and theoretical data of the first-degree polynomial model ET1 and the second-degree equation model ET2 are perfectly matched with each other. Data indicate error of ET1 can even be 0.001K, and ET2 can be 0.1K. It can be predicted that under higher signal-noise ratios, the third-degree equation polynomial model ET3 can alfacilitate any preset precision.

This indicates temperature measurement method based on superparamagnetism for a magnetic nanoparticle is feasible in theory.

The polynomial approximation model exhibits comparatively small system error, this is because it nonlinearly corrects the magnetization process based on the linear approximation model. A magnetic test system is to face thermal noise or external interruption under small magnetic excitation, and thus it is difficult to ensure precision of low-field test. During the test process, it is normally expected to effectively reduce interruption of noise by increasing excited magnetic field. Under comparatively large excited magnetic field, if only a linear model is used, obvious system error is to occur, as shown in FIG. 1. Increase of a saturation magnetic moment leads to occurrence of system error, as shown in FIG. 2. In the linear model, it is found that nonlinearity of the saturation magnetic moment (or the excited magnetic field) leads to obvious zero shift and variation of a slope, which are system errors. A method to correct the system error is to use polynomial approximation. Comparatively, the polynomial model well processes nonlinearity of the magnetization process, and generates no obvious error under comparatively large magnetic excitation (or saturation magnetic moment). By using the polynomial method, a saturation magnetic moment M can be obtained via multiple times of measurement under known temperature condition. Practical tests indicate saturation magnetic moment after multiple times of measurement is comparatively stable.

As noise cannot be neglected, different degrees in the polynomial approximation model directly affect suppression of noise. Degree of the polynomial model during test is 1 to 3. It can be seen from prediction algorithms of the first-degree, the second-degree, and the third-degree models in FIGS. 4-6 that, under the same precision, as the degree of the algorithm is increased by 1, a signal-noise ratio of a temperature prediction result thereof correspondingly is reduced by 40 dB to 50 dB. This indicates noise suppression capability is the best. With increase of the degree of the algorithm, noise suppression capability gradually weakens. Therefore, noise suppression capability of the third-degree algorithm or above is very poor, and cannot be used in temperature prediction. In this context, only the first-degree algorithm is considered, and a repeated experiment of the first-degree polynomial approximation algorithm containing noise is shown in FIG. 7. In addition, in terms of random interference during measurement, higher precision can be obtained by multiple times of repeated measurement.

3) Practical Test and Analysis

Figure 8:
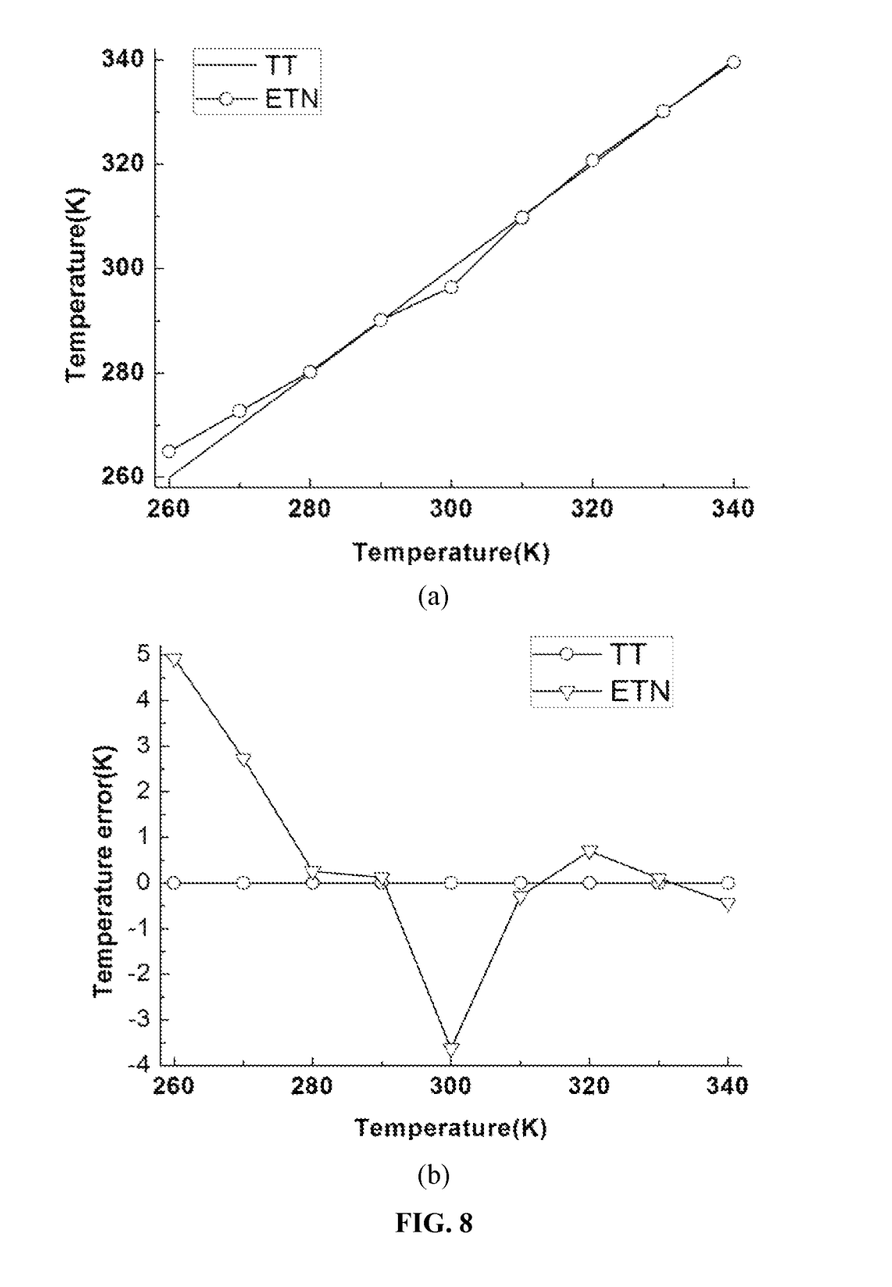
FIG. 8 illustrates actual test results at different temperature ranges.
Figure 9:
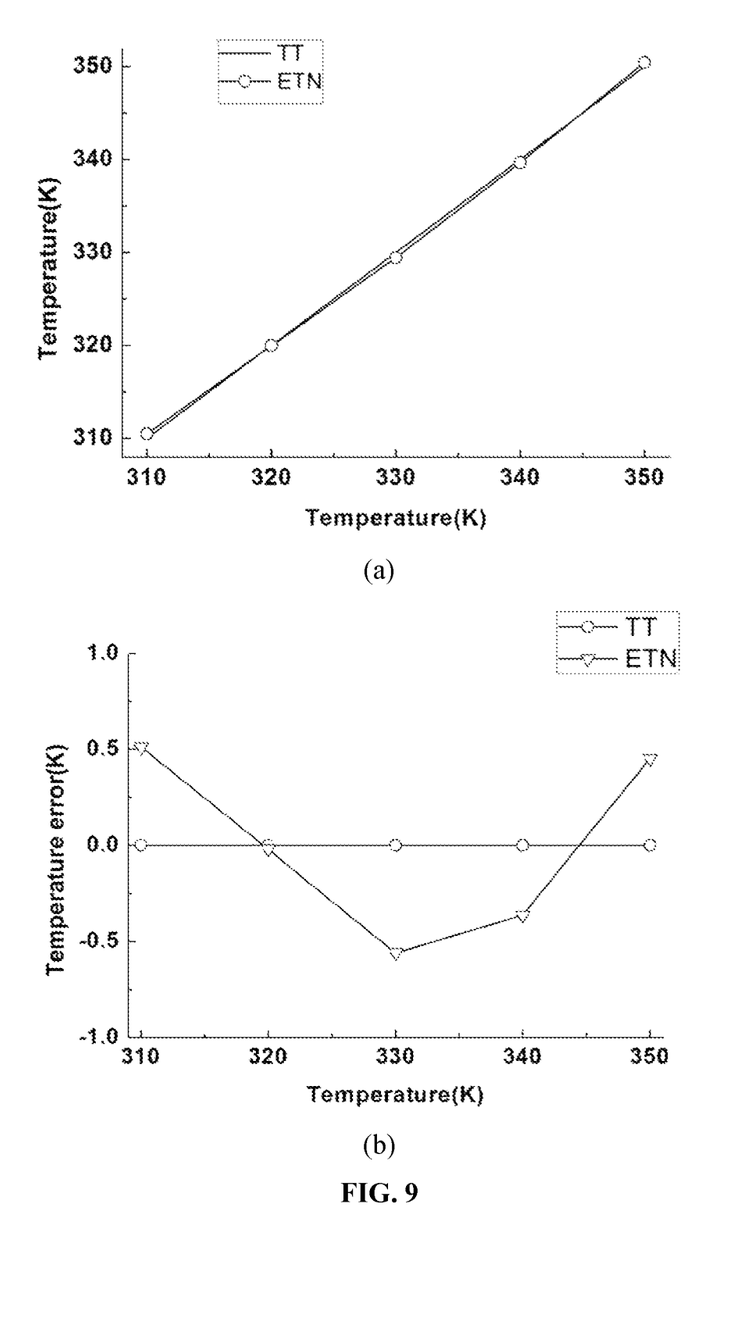
FIG. 9 illustrates temperature test results after repeating 9 times of experiments of a sample.

To prove applicability of the above-mentioned model in practical precision measurement, magnetic nano solid particle EMG1400 (FerroTec, USA) samples are used. A measurement instrument is a SQUID VSM (Quantum Design, USA) magnetometer. Based on multiple times of measurement and analysis, system parameters are adjusted to the optimum state and thus a final experiment scheme is determined. Excited magnetic field during the experiment is set to −200 Gs-+200 Gs, and every 5 Gs is one point. Temperature range of FIG. 8 is 260K-340K, and every 15K is one temperature point. Taken temperature stability of the MPMS device at low temperature section into account, experiment data above room temperature are given in FIG. 9. Temperature range in FIG. 9 is 310K-350K, and every 10K is one temperature point.

Figure 10:
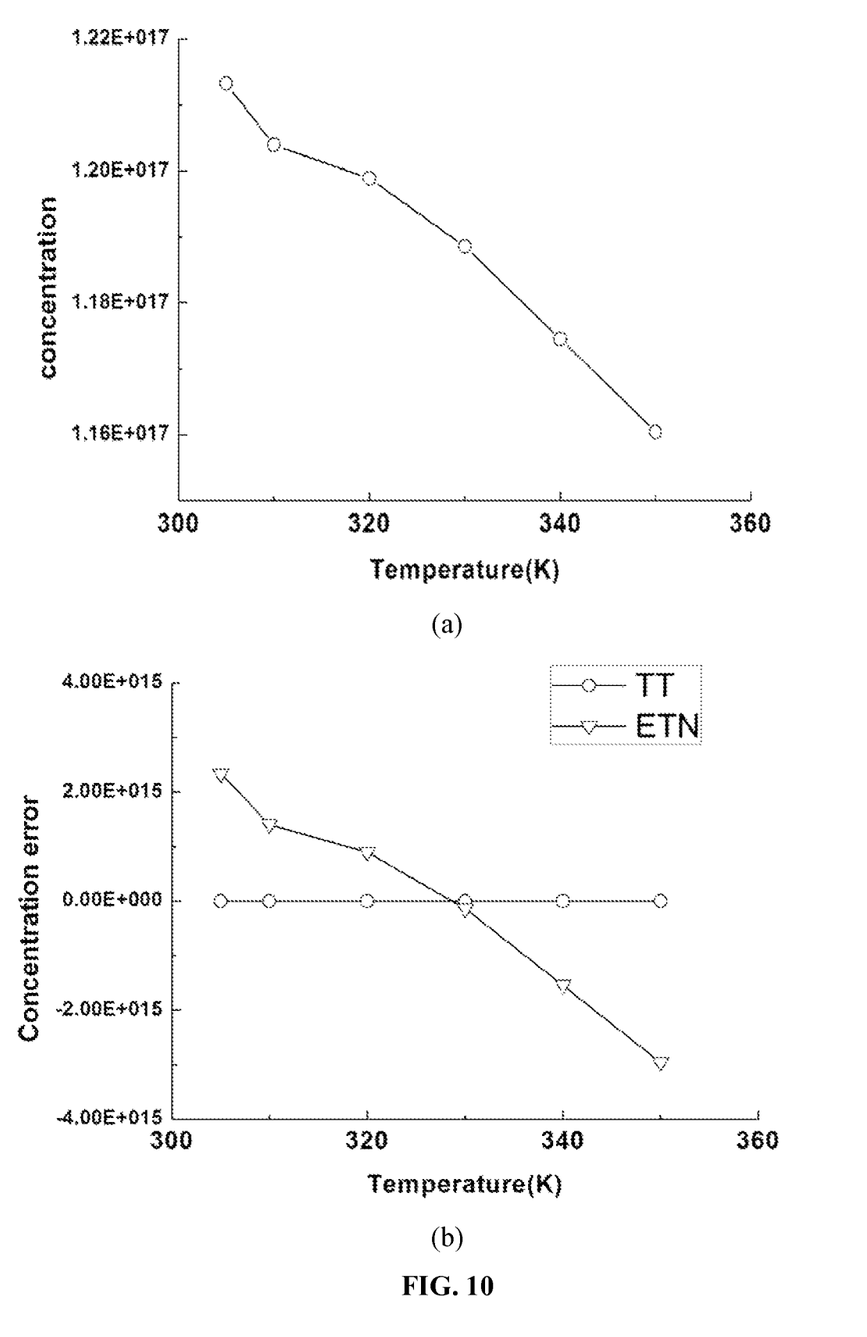
FIG. 10 illustrates test results and actual results of a concentration parameter N at different temperature, FIG. 10(a) are test results of the concentration parameter N at different temperature.

Problems with the practical data are that undetermined factors exist in the saturation magnetic moment M in equations $$\begin{cases} MN = \dfrac{1}{\sqrt{xy}} = \dfrac{a}{\sqrt{b}} \\ \dfrac{T}{M} = \dfrac{1}{K}\sqrt{\dfrac{x}{y}} = \dfrac{1}{k\sqrt{b}}, \end{cases}$$

and cannot be known in advance. Different agglomeration states in different environments of the same sample, such as dimer, trimer, or mulltimer, are to affect the saturation magnetic moment. Therefore, off-line measurement of the saturation magnetic moment may fail, and accordingly the actual temperature cannot be obtained accurately. An engineering-oriented method is to use magnetic susceptibility data of a group of known temperature to calculate an average M, and then to substitute M in the equations $$\begin{cases} MN = \dfrac{1}{\sqrt{xy}} = \dfrac{a}{\sqrt{b}} \\ \dfrac{T}{M} = \dfrac{1}{K}\sqrt{\dfrac{x}{y}} = \dfrac{1}{k\sqrt{b}} \end{cases}$$

as a known quantity. This makes it convenient to operate during practical application.

actual experiment data using the above-mentioned test method indicate that, although error during single temperature measurement is comparatively large, after multiple times of measurement, the measurement error can be less than 1K. FIG. 8(a) provides a preset (theoretical) temperature value TT and a measured temperature value ETN of single measurement, and FIG. 8(b) provides temperature error of the single measurement. FIG. 9(a) provides average temperature value after nine times of repeated measurement, and FIG. 9(b) provides difference between the average value and the theoretical preset value. Experiment data indicate the maximum error after 9 times of repeated measurement is 0.56K. The variance of single measurement is 1.66-1.03, a root mean square of average temperature of nine times of repeated measurement is the result in FIG. 9(b) divided by 3($\sqrt{9}=3$). Therefore, temperature measurement using the above-mentioned method has a root mean square of 0.34K-0.55K after 9 times of measurement. In addition, the first-order polynomial approximation model can be used for remote measurement of concentration. Measurement error of concentration under different temperature is less than 3%, as shown in FIG. 10. Advantages of the first-order polynomial approximation model method are that small magnetic excitation is used, and thus measurement of particle concentration can be implemented without superconductive magnetic field.

The invention claimed is:

1. A method for paramagnetism-based remote temperature measurement of a measured object using magnetic nanoparticles, comprising:
    (1) positioning a sample of said magnetic nanoparticles at an area of said measured object;
    (2) applying n times of different excited magnetic fields on said area, where n≧2;
    (3) collecting magnetization of said sample under said different excited magnetic fields, and detecting magnetic susceptibility of said sample under said different excited magnetic fields according to said magnetization;
    (4) constructing equations between said magnetic susceptibility and said different excited magnetic fields $$\frac{1}{\chi_i} = \frac{H_i}{NML\left(\frac{MH_i}{kT}\right)},$$
$$i = 1, 2 \ldots n,$$

wherein;

$\chi_i$ is said magnetic susceptibility; $H_i$ is said different excited magnetic fields; reciprocal of the Langevin's function $$L\left(\frac{MH_i}{kT}\right): \frac{1}{L(\alpha)} = \sum_{j=0}^{J} c_{2j-1}\alpha^{2j-1};$$
$$\alpha = \frac{MH_i}{kT};$$

$c_{2j-1}$ is a polynomial coefficient; J+1 is a predetermined polynomial expansion term; N is concentration of said sample; M is atomic magnetic moment of said sample; k is a Boltzmann's constant; and T is temperature of said measured object;

5) solving said equations, using a processor, to obtain said temperature T, wherein J=1, and step (5) comprises:

using a linear equation $$\frac{1}{\chi_i} = 3x + \frac{1}{5}H_i^2 y$$

to perform curve fitting on a sequence point $$\left(H_i^2, \frac{1}{\chi_i}\right);$$

and calculating said temperature according to an intercept 3x and a slope $$\frac{1}{5}y$$

of a straight line obtained by said curve fitting:

$$T = \frac{M}{k}\sqrt{\frac{x}{y}}.$$

2. The method of claim 1, wherein step (5) further comprises calculating said concentration of said sample $$N = \frac{1}{M\sqrt{xy}}.$$

3. A method for paramagnetism-based remote temperature measurement of a measured object using magnetic nanoparticles, comprising:

(1) positioning a sample of said magnetic nanoparticles at an area of said measured (2) applying n times of different excited magnetic fields on said area;

(3) collecting magnetization of said sample under said different excited magnetic fields, and calculating magnetic susceptibility of said sample under said different excited magnetic fields according to said magnetization;

(4) constructing equations between said magnetic susceptibility and said different excited magnetic fields $$\frac{1}{\chi_i} = \frac{H_i}{NML\left(\frac{MH_i}{kT}\right)},$$
$$i = 1, 2 \ldots n,$$

wherein;

$\chi_i$ is said magnetic susceptibility; $H_i$ is said different excited magnetic fields; reciprocal of the Langevin's function $$L\left(\frac{MH_i}{kT}\right): \frac{1}{L(\alpha)} = \sum_{j=0}^{J} c_{2j-1}\alpha^{2j-1};$$
$$\alpha = \frac{MH_i}{kT};$$

$c_{2j-1}$ is a polynomial coefficient; J+1 is a predetermined polynomial expansion term; N is concentration of said sample; M is atomic magnetic moment of said sample; k is a Boltzmann's constant; and T is temperature of said measured object;

(5) solving said equations, using a processor, to obtain said temperature T, wherein J≧2 and step (5) comprises (51) transforming said equations between said magnetic susceptibility and said excited magnetic fields into a matrix equation $$\begin{bmatrix} \frac{1}{\chi_1} \\ \frac{1}{\chi_2} \\ \vdots \\ \frac{1}{\chi_n} \end{bmatrix} = A \cdot \begin{bmatrix} \frac{1}{a} \\ \frac{b}{a} \\ \vdots \\ \frac{b^{Q-1}}{a} \end{bmatrix},$$

wherein:

$$\begin{cases} a = \frac{M^2 N}{kT} \\ b = \frac{M^2}{k^2 T^2}; \end{cases}$$

1≦Q≦J+1; and A is a coefficient matrix;

(52) solving equations $$\begin{cases} \dfrac{b^{q-1}}{a} = A_q^* \cdot \left[ \dfrac{1}{\chi_1} \quad \dfrac{1}{\chi_2} \quad \cdots \quad \dfrac{1}{\chi_n} \right]^T, q = 1 \\ \dfrac{b^{q-1}}{a} = A_q^* \cdot \left[ \dfrac{1}{\chi_1} \quad \dfrac{1}{\chi_2} \quad \cdots \quad \dfrac{1}{\chi_n} \right]^T, 2 \le q \le Q \end{cases}$$

to obtain a and b, wherein $A_q^*$ is the $q^{th}$ row of a generalized inverse of said coefficient matrix A; and (53) calculating said temperature of said measured object;

$$T = \frac{M}{k\sqrt{b}}.$$

4. The method of claim 3, wherein step (5) further comprises calculating said concentration of said sample:

$$N = \frac{a}{M\sqrt{b}}.$$

5. A method for paramagnetism-based remote temperature measurement of a measured object using magnetic nanoparticles, comprising:
(1) positioning a sample of said magnetic nanoparticles at an area of said measured
(2) applying n times of different excited magnetic fields on said area;
(3) collecting magnetization of said sample under said different excited magnetic fields, and calculating magnetic susceptibility of said sample under said different excited magnetic fields according to said magnetization;
(4) constructing equations between said magnetic susceptibility and said different excited magnetic fields $$\frac{1}{\chi_i} = \frac{H_i}{NML\left(\frac{MH_i}{kT}\right)},$$

$$i = 1, 2 \ldots n,$$

wherein:
$\chi_i$ is said magnetic susceptibility; $H_i$ is said different excited magnetic fields; reciprocal of the Langevin's function $$L\left(\frac{MH_i}{kT}\right): \frac{1}{L(\alpha)} = \sum_{j=0}^{J} c_{2j-1} \alpha^{2j-1};$$

$$\alpha = \frac{MH_i}{kT};$$

$c_{2j-1}$ is a polynomial coefficient; J+1 is a predetermined polynomial expansion term; N is concentration of said sample; M is atomic magnetic moment of said sample; k is t Boltzmann's constant; and T is temperature of said measured object;

(5) solving said equations, using a processor, to obtain said temperature T, wherein $2 \le J \le 5$ and step (5) comprises:

(51) transforming said equations between said magnetic susceptibility and said excited magnetic fields into a matrix equation $$\begin{bmatrix} \dfrac{1}{\chi_1} \\ \dfrac{1}{\chi_2} \\ \vdots \\ \dfrac{1}{\chi_n} \end{bmatrix} = A \cdot \begin{bmatrix} \dfrac{1}{a} \\ \dfrac{b}{a} \\ \vdots \\ \dfrac{b^{Q-1}}{a} \end{bmatrix},$$

wherein:

$$\begin{cases} a = \dfrac{M^2 N}{kT} \\ b = \dfrac{M^2}{k^2 T^2}; \end{cases}$$

$1 \le Q \le J+1$; and A is a coefficient matrix;

(52) solving equations $$\begin{cases} \dfrac{b^{q-1}}{a} = A_q^* \cdot \left[ \dfrac{1}{\chi_1} \quad \dfrac{1}{\chi_2} \quad \cdots \quad \dfrac{1}{\chi_n} \right]^T, q = 1 \\ \dfrac{b^{q-1}}{a} = A_q^* \cdot \left[ \dfrac{1}{\chi_1} \quad \dfrac{1}{\chi_2} \quad \cdots \quad \dfrac{1}{\chi_n} \right]^T, 2 \le q \le Q \end{cases}$$

to obtain a and b, wherein $A_q^*$ is the $q^{th}$ row of a generalized inverse of said coefficient matrix A; and (53) calculating said temperature of said measured object;

$$T = \frac{M}{k\sqrt{b}}.$$

6. The method of claim 5, wherein step (5) further comprises calculating said concentration of said sample:

$$N = \frac{a}{M\sqrt{b}}.$$

* * * * *